US008445671B2

(12) United States Patent
Dvořák et al.

(10) Patent No.: US 8,445,671 B2
(45) Date of Patent: May 21, 2013

(54) METHOD FOR PREPARING POLYANHYDROGLUCURONIC ACID AND/OR SALTS THEREOF (75) Inventors: Radim Dvořák, Tišnov (CZ); Jiři Briestensky, Černilov (CZ); Ivan Santar, Strakonice (CZ); Anthony Richardson, Killiney (IE)

(73) Assignee: Alltracel Development Services Limited, County Dublin (IE)

( * ) Notice: Subject to any disclaimer, the term of this patent is extended or adjusted under 35 U.S.C. 154(b) by 729 days.

(21) Appl. No.: 11/991,153

(22) PCT Filed: Sep. 1, 2006

(86) PCT No.: PCT/IE2006/000093
§ 371 (c)(1),
(2), (4) Date: Feb. 28, 2008

(87) PCT Pub. No.: WO2007/026341
PCT Pub. Date: Mar. 8, 2007

(65) Prior Publication Data
US 2009/0043089 A1 Feb. 12, 2009

Related U.S. Application Data (60) Provisional application No. 60/713,334, filed on Sep. 2, 2005.

(51) Int. Cl.
*C08B 37/00* (2006.01)
(52) U.S. Cl.
USPC .......................................................... 536/124
(58) Field of Classification Search
USPC .......................................................... 536/124
See application file for complete search history.

(56) References Cited

U.S. PATENT DOCUMENTS

| | | | |
|---|---|---|---|
| 4,100,341 A | 7/1978 | Brasey et al. | |
| 4,347,057 A | 8/1982 | Yasnitsky et al. | |
| 5,134,229 A * | 7/1992 | Saferstein et al. | 536/56 |
| 6,127,573 A | 10/2000 | Li et al. | |
| 2003/0077231 A1 | 4/2003 | Santar et al. | |

FOREIGN PATENT DOCUMENTS

| | | |
|---|---|---|
| CS | 185366 | 9/1978 |
| DE | 941282 | 4/1956 |
| DE | 967144 | 10/1957 |
| EP | 0492990 | 7/1992 |
| EP | 0659440 | 6/1995 |
| GB | 709684 | 6/1954 |
| GB | 1593513 | 7/1981 |
| JP | 2003-321398 | 11/2003 |
| JP | 2004-002586 | 1/2004 |
| JP | 2004-059618 | 2/2004 |
| SU | 937462 | 6/1982 |
| WO | 98/00446 | 1/1998 |
| WO | 9833822 | 8/1998 |
| WO | WO 98/33822 * | 8/1998 |

OTHER PUBLICATIONS

Saito et al, Biomacromoleucles, 2004, 5, 1983-89.*
International Search Report, dated Oct. 16, 2006.
Burchard; "Polysaccharide in der Pharmazie", *Eigenschaften and Nutzung*; Springer-Verlag, Berlin, 1985, pp. 140-141.
Kenyon et al.; "Oxidation of Cellulose; A Staff-Industry Collaborative Report . . . "; *Industrial and Engineering Chemistry*, vol. 41, No. 1; Jan. 1949; pp. 2-8.
Painter et al.; "New Glucuronoglucans Obtained by Oxidation of Amylose at Position 6"; *Carbohydrate Research*, No. 140; 1985 Elsevier Science Publishers, B.V.; pp. 61-68.
Alhaique et al.; "Oxidized scleroglucan for the design of a pH-controlled drug delivery system"; *Chimicaoggi- luglio-agosio*, 1986; pp. 11-15.
Kaversneva; *Doklady AN SSSR* (U.S.S.R.), vol. 78 No. 3, 1951; pp. 481-483.
Nevell; "The Oxidation of Cotton Cellulose by Nitrogen Dioxide"; *The Journal of the Textile Institute*, Mar. 1951; pp. T91-T129.
Sihtola et al; "Classification of Carbonyl Groups in Cellulose on the Basis of their Reaction Rates at Oximation"; *Journal of Polymer Science: Part C*, No. 2, 1963; pp. 289-309.
Passteka; *Chentické Zvesti* (Slovakia), No. 20; 1966; pp. 855-861.
Saito et al.; "TEMPO-Mediated Oxidation of Native Cellulose. The Effect of Oxidation Conditions on Chemical and Crystal Structures of the Water-Insoluble Fractions"; *Biomacromolecules* 2004, No. 5; American Chemical Society; pp. 1983-1989.
Li et al.; Oxidation of primary alcohols to carboxylic acids with a *TEMPO* catalyst using NaClO$_2$ and NaClO. (U.S. Patent 6,127,573, Document AD.).

* cited by examiner

*Primary Examiner* — Shaojia Anna Jiang
*Assistant Examiner* — Ganapathy Krishnan
(74) *Attorney, Agent, or Firm* — Jacobson Holman PLLC (57) ABSTRACT

A method for preparing polyanhydroglucuronic acid and/or salts thereof is described. A polyanhydroglucuronic acid-containing material obtained by oxidation is subjected to partial or complete hydrolysis to form a homogeneous system, subsequent ion exchange in the homogeneous system; and supplemental oxidation in the presence of any one or more of organic and inorganic peroxides.

15 Claims, 3 Drawing Sheets

Figure 1:
*Schematic representation of the process of the invention (Cold Process)*

Figure 2:
*Particle size distribution for a number of batches prepared using the process of the invention*

Figure 3:
*Comparison of particle size distrubution for product prepared using the process of the invention (Cold Process) in comparison to product prepared using two different versions of "hot process technology" (Comparative Methods I, II)*

METHOD FOR PREPARING POLYANHYDROGLUCURONIC ACID AND/OR SALTS THEREOF

This is a national stage of PCT/IE2006/000093 filed on Sep. 1, 2006 and published in English, claiming benefit of U.S. provisional application No. 60/713,334, filed on Sep. 2, 2005.

The invention relates to a method for preparing a product comprising polyanhydroglucuronic acid (PAGA) and salts thereof and to the uses thereof. The products are especially suitable for medicinal, pharmaceutical and cosmetic products. The term polyanhydroglucuronic acid and salts thereof as used herein includes copolymers thereof, especially with anhydroglucose.

INTRODUCTION

Besides proteins, polysaccharides represent the most widespread biopolymers found in the biosphere. As an example, up to $10^{12}$ metric tonnes per year of cellulose, a 1,4β D-glucane, is synthesized in nature. Other α and β glucanes bound e.g. by 1,2; 1,3; 1,4 and 1,6; or 1,2 and 1,4 glycosidic bonds in the main chain, mostly of microbial origin, gain increasing importance with ongoing research in the field. It is the presence of glucuronic acid units in the polymeric chain of the oligosaccharides or polysaccharides that, together with their molar mass and type of the principal glycosidic bond, constitutes the basis of their immunostimulative, antitumourous, anticoagulative, or else haemostyptic effects (1).

Glucuronoglucanes can preferably be prepared by relatively specific selective oxidation of the primary alcoholic group at C6 carbon atom of the glucopyranosic unit of natural polysaccharides by nitrogen oxides, the C1 aldehydic group of the basic unit being protected by the glycosidic bond.

A variety of methods have been disclosed for preparing glucuronoglucanes and glucuronanes from natural glucanes, using the oxidative effects of $NO_X$ either in the gaseous form (2, DE 0941282; DE 0967144), in nonpolar reaction environment of inert liquids such as hydrogenated hydrocarbons (USSR SU 937462; U.S. Pat. No. 4,347,057; EP 0492990), or in polar environment of aqueous solutions of acids such as $HNO_3$, $H_3PO_4$ or their mixtures with $HSO_4$, wherein the $NO_X$ are mostly generated directly in the oxidation liquor via dosed introduction of reducing substances such as, notably, $NaNO_2$ (GB 709684; CS AO 185366; GB 1593513; (3), (4)), or the reaction environment is created by introducing liquid $NO_X$ into aqueous $HNO_3$ (U.S. Pat. No. 4,100,341).

A disadvantage of these processes relates to the fact that their oxidative effects on the glucane molecule are non-uniform and only relatively specific in that besides creation of carboxyl groups of the uronic type of C6 carbon of the glucopyranosic unit, other types of successive reactions (such as formation of $ONO_2$ and NO groups on C6) and secondary reactions (such as formation of COOH and other oxidised groups on end carbons C1 and C4, and notably on C2 and C3 carbons) do occur. In accordance with numerous publications (5, 6, 7, 8), extensive testing of polyanhydroglucuronic acids prepared by the action of $NO_X$ has led us to the conclusion that, besides carboxyl groups on C6 carbon, several other aldehydes, ketones, and their condensation products are formed that have fundamental influence on the stability of the polyanhydroglucuronic acid product.

In recent years ((9, 10) and U.S. Pat. No. 6,127,573) a new method for oxidation of polysaccharides, called the TEMPO method, consisting in that the oxidation on the C6 carbon by sodium hypochlorite is catalysed by 2,2,6,6-tetramthylpiperidine-1-oxyl radical in the presence of bromide ions. A disadvantage of this method, similar to oxidation by $NO_X$, is again the high product non-homogeneity due to heterogeneous reaction, notably in crystalline regions.

It is evident from the above that the preparation of stable PAGA product having required physical and chemical characteristics, destined for pharmaceutical and cosmetic use, is in no way a simple matter.

In health care practice one often encounters cases of capillary bleeding occurring during injuries or related to surgical interventions. The healing of the wounds frequently depends on attaining rapid homeostasis and creation of coagulum, to especially serve as a protection of the wound against infection. Application of D glucurono-1,4β D-glucane, the so-called oxidised cellulose, as a non-toxic resorbable local haemostatics to arrest bleeding from surface injuries or parenchymatous organs, osseous bleeding, and in general wherever use of conventional styptic means may be difficult or slow in functioning and less effective, has proved especially effective in similar cases.

Other disadvantages of the known methods described above are the non-uniform degree of both oxidation and degradation of individual polysaccharide particles or fibres, non-uniform content of bound nitrogen and other destabilizing sites in the macromolecule, as well as broad distribution of their molecular masses, altogether factors which can result in non-uniformity in resorbtion in the organism on applying the product as a haemostatic or in binding other substances or drugs such as anaesthetics, antibiotics or cytostatics.

WO98/33822 describes a method for preparing stable polyanhydroglucuronic acid with controlled physicochemical properties adapted to the intended use, thus reducing or fully suppressing deficiencies of conventional products manufactured as well as broadening the potential scope of applications thereof. A lot of the deficiencies described above are overcome by WO98/33822. Stabilized microdispersed PAGA is prepared with a reduced degree of crystallinity, its copolymers with anhydroglucose, and salts thereof, with a high degree of purity. The stable microdispersed PAGA prepared has easily controllable physicochemical characteristics.

Any improved method for the preparation of an oxidised cellulose product would have wide application.

STATEMENTS OF INVENTION

According to the invention there is provided for preparing polyanhydroglucuronic acid and/or salts thereof comprising the steps of:
  hydrolysis of a polyanhydroglucoronic acid-containing material to form a substantially homogeneous system; and
  subsequently subjecting the product of the hydrolysis step to ion exchange.

In one embodiment the polyanhydroglucoronic acid-containing material is obtained by oxidation of a suitable polysaccharide.

In one embodiment the polyanhydroglucuronic acid-containing material is obtained by oxidation with nitrogen oxides or using sodium hypochorite in the presence of a TEMPO catalyst.

In one embodiment the method comprises supplemental oxidation of the product of the ion exchange step in the presence of one or more of organic and inorganic peroxides.

In one aspect the invention there is provides a method for preparing a product comprising polyanhydroglucuronic acid and/or salts thereof wherein a polyanhydroglucuronic acid-containing material obtained by oxidation of a suitable polysaccharide is subjected to the following:

partial or complete hydrolysis in an aqueous system;
ion exchange; and
supplemental oxidation in the presence of any one or more of organic and inorganic peroxides The process may be carried out in an aqueous system which may comprise an admixture of an organic solvent. The organic solvent may be selected from any one or more of ethanol, isopropanol or other water-miscible alcohol or organic solvents.

In one embodiment the aqueous system comprises at least one inorganic and/or organic salt and/or base. The inorganic and/or organic salts and/or bases may be selected from any one or more of chlorides, sulphates, carbonates, formates, acetates of alkali and/or alkaline earth metals, hydroxides of alkali and/or alkaline earth metals, alkylamines and alkanolamines, in concentrations ranging from 0.001 to 5 mol/l.

In one embodiment the ion exchange step is carried out in the presence of water soluble and/or partially soluble inorganic/organic salts or bases. The inorganic and/or organic salts and/or bases may be selected from any one or more of hydroxides, chlorides, nitrates, borates, sulphides, sulphates and acetates.

The method may be carried out at a temperature between −5° C. and 50° C., preferably at a temperature of 15 to 30° C.

In one embodiment hydrolysis is carried out for a period of about 15 to about 30 minutes.

Ion exchange may be carried out for a period of about 15 to about 30 minutes.

In one case the supplemental oxidation is carried out for a period of about 15 to about 30 minutes.

In one embodiment the method includes the step of precipitating, washing and drying the product.

The method may include the step of dehydrating the product. The pH may be adjusted to between 2.0 and 8.5 prior to precipitation. The product may be washed and/or dehydrated, using suitable water miscible or partially miscible organic solvents and/or converted, in an appropriate manner, for intended subsequent use.

The product may be dried at a temperature of between 20 and 105° C. After drying, the product may be milled and/or sieved.

In one embodiment an oxidative environment during supplemental oxidation is established by the presence of oxidising agents selected from one or more of hydrogen, sodium or magnesium peroxide, peroxoacids and their salts, hypochlorites and chlorites.

The polyanhydroglucuronic acid-containing material may be obtained by oxidation of a suitable polysaccharide, including native or regenerated cellulose or starch.

The invention also provides stable microdispersed polyanhydroglucuronic acid and salts thereof wherever prepared by a method of the invention.

The stable microdispersed polyanhydroglucuronic acid and salts thereof may contain in their polymeric chain from 8 to 30 percent by weight of carboxyl groups, at least 80 percent by weight of these groups being of the uronic type, at most 5 percent by weight of carbonyl groups, and at most 0.5 percent by weight of bound nitrogen.

The molecular mass of the polymeric chain may range from $1 \times 10^3$ to $8 \times 10^5$ Daltons.

The bulk volume of the product may range from 0.5 to 30 ml per gram.

The specific surface area of the product may range from 0.3 to 200 $m^2$ per gram.

The invention also provides a pharmaceutical, cosmetic or nutraceutical composition incorporating a product comprising polyanhydroglucuronic acid and/or salts thereof or prepared by a method of the invention.

The composition may include at least one biocompatible biologically active substance.

The composition may include at least one biologically acceptable adjuvant.

According to the invention there is provided a method for preparing a product comprising polyanhydroglucuronic acid and/or salts thereof wherein a polyanhydroglucuronic acid-containing material obtained by oxidation is subjected to the following:

partial or complete hydrolysis (or, in other words, neutralization or dissolution) in an aqueous system;
ion exchange; and
supplemental oxidation in the presence of any one or more of organic and inorganic peroxides

BRIEF DESCRIPTION OF THE DRAWINGS

The invention will be more clearly understood from the following description thereof given by way of example only with reference to the accompanying drawings in which:—

DETAILED DESCRIPTION

We have found an improved oxidative ion-exchange hydrolysis (cold process) method for preparing an oxidised cellulose product which has significant advantages over other known processes, in particular over the process described in WO98/33822, which is also referred to as the oxidative hydrolysis (hot process) and hereinafter referred to as Comparative Method I or II.

Figure 1:
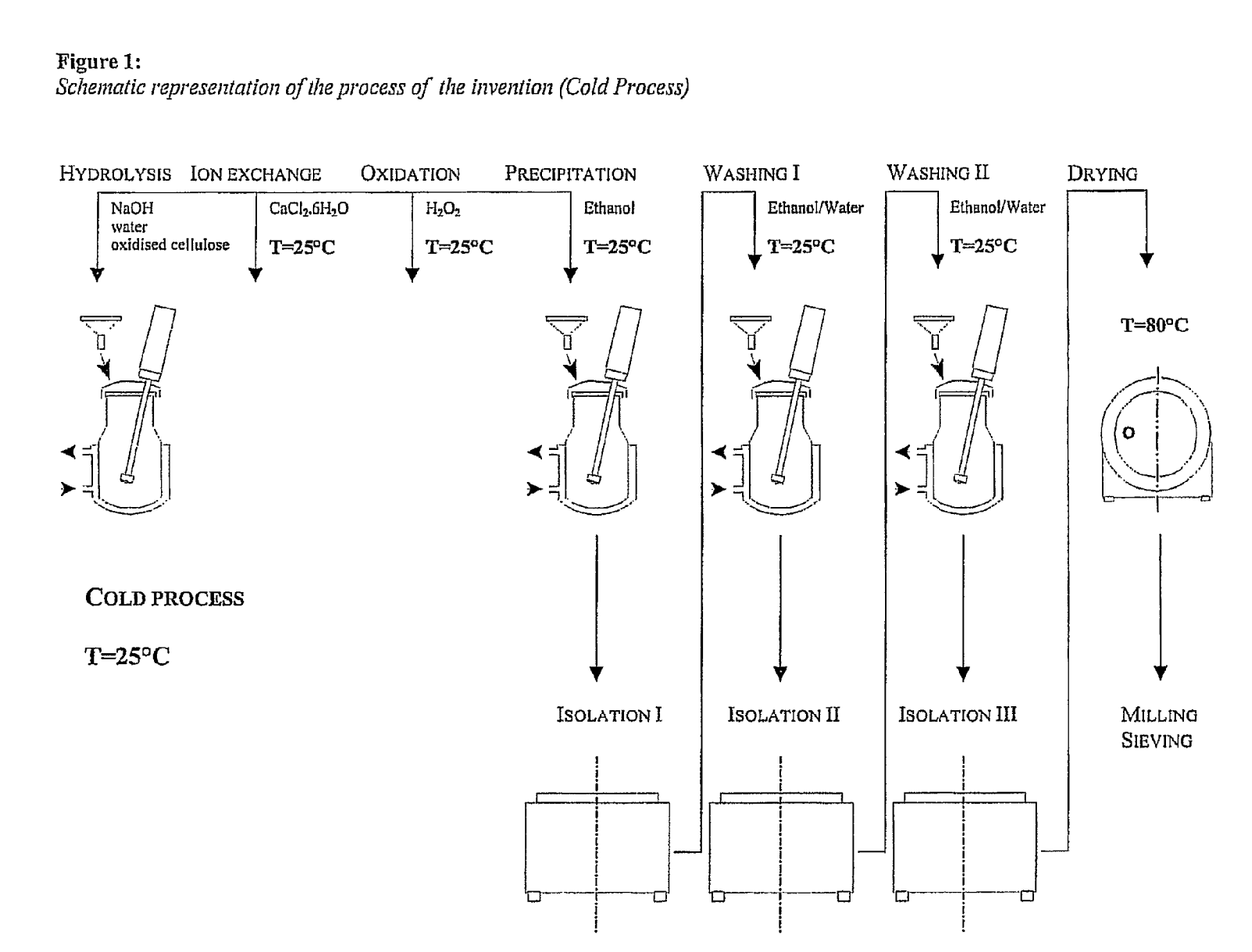
FIG. 1 is a schematic representation of the process of the invention.

The method of the invention involves the transformation of oxidised cellulose (OC) to their salts from an excess of water soluble hydroxide, salt or organic base such as NaOH, KOH, LiOH, $NH_4OH$, $Na_2CO_3$, and $R—NH_2$. Oxidised cellulose in hydroxide (salt, organic base) solution is fully dissolved and a corresponding salt of OC is formed. Ion-exchange is performed using inorganic and/or organic water soluble salts or bases (such as chloride, nitrate, carbonate, sulphate etc.) with a different type of cation and a double salt of OC is formed. Part of the original ions are thereby changed to an OC salt of the new cation. The ion exchange is fully controlled by the amount of inorganic and/or organic salt used. Oxidation, precipitation, washing, dehydration in water miscible or partially miscible organic solvents when necessary, and drying are subsequently performed.

The cold process of the invention involves a more homogenous reaction system in contrast to the fully heterogenous system of the Comparative Methods I and II. All the steps involved can be carried out at temperatures between −10 and 50° C., preferably at 25° C.

In addition an admixture of an organic solvent (such as EtOH, isopropanol or other water miscible alcohol or organic solvents) is added to the aqueous system before or during hydrolysis, thereby shifting the range of applicable reaction temperatures down to below 50° C. and decreasing the heat capacity of the reaction system to achieve energy savings.

By way of an example, the reaction scheme for preparation of for example a sodium/calcium salt is outlined as follows:

1. hydrolysis (sodium salt of OC is formed)

2. ion exchange (mixture of both salts is formed=MDOC Ca/Na)

3. oxidation (oxidation of residual terminal $CH_2OH$ and/or carbonyl groups, which are present in input raw material)

4. adjustment of pH (removal of excess of alkaline entities)

Oxidised cellulose is a copolymer of:

where:

(A) = $R^{OC}$—COOH
(B) = $R^{OC}$—$CH_2OH$

The cold process of the invention results in high yields, uniform colour of the final product and zero inorganic carbonates content as there is no source of carbonates in the reaction process. Unreacted inorganic carbonates are undesirable side products which are formed using other methods such as Comparative Method I or II. Moreover the risk of the presence of raw cellulose and/or unreacted oxidised cellulose fibres, which may have adverse effects for some applications of the product, in particular for internal applications, is decreased because the mixture can be filtered after the neutralization due to its being homogenous.

The process provides a number of advantages over other known processes for preparing oxidized cellulose including shorter production times (less than 7 hours) and lower production costs resulting in greater energy savings. In addition the content of cations in the final product is better controlled using appropriate weighing of the salts used. The method also results in a lighter colour of the powder being formed thus enhancing the appearance of final products and in a narrower particle size distribution. The latter is especially important for aerosol packaging of the product.

FIG. 1 provides a schematic outline of the cold process of the invention. Hydrolysis takes place at temperatures between −10 to +50° C., preferably at 25° C. Ion exchange and oxidation take place at the same temperature. The pH of the reaction mixture is adjusted to a value between 2.0 to 9.5 using mineral or organic acid depending on the pH required for the final product. After adjusting the pH, the reaction mixture is precipitated by a water-miscible organic solvent and the isolated filter cake is treated by repeated washing as required in suitable water/organic solvent mixtures for removal of residual inorganic salts. The solvent mixtures may involve EtOH/water, concentrated ethanol, isopropanol, methylal or other ethers depending on the required particle size for the final product. Finally the isolated wet product is dried at 25 to 100° C. depending on dryer used or milled and/or sieved if required.

As a result, fibres of oxidised cellulose are transformed into a microdispersed oxidised cellulose (MDOC) (such as a sodium-calcium salt of MDOC). This microdispersed form having haemostatic, antibacterial and/or other useful properties may be used in further processing (such as spray or plaster etc. manufacture).

We have preferably concentrated on two forms of microdispersed oxidised cellulose (MDOC) called powder (MDOC I) and granulate (MDOC II), respectively. MDOC I is a powder used mainly for aerosol can filling and MDOC II is used as a haemostatic agent in wound pads and plasters. Both products have the same chemical composition and differ from each other only in particle size. While MDOC I has to have maximum particle size of powder of 50 μm to go through a spray valve, MDOC II is produced in agglomerate form because the subsequent processing of the product is typically performed by a dry method and processed MDOC II should not give rise to excessive dusting and requires minimum particle size to be kept above 100 μm.

After the drying of MDOC in both cases agglomerates of primary particles are obtained. If required, the agglomerates are further milled and in the case of MDOC II sieved as well. Agglomerates of MDOC I are fine and soft and by milling very small particles (in units of μm) are obtained, in comparison to MDOC II agglomerates, which are very hard and brittle. This is as a result of the water content in the final filter cake (i.e. in the filter cake before drying). While in the case of MDOC I ideally a filter cake without water is required, in the case of MDOC II a water content of at least 5 to 75% w/w is required. Therefore the water present in the last filter cake has a strong effect on the agglomerates formed and their nature.

The MDOC prepared by the method of the invention may be used in pharmaceutical or cosmetic compositions as described in WO98/33822 the entire contents of which are herein incorporated.

The invention will be more fully understood from the following description given by way of example.

EXAMPLES

The method of the invention is termed a "cold process technology". In comparison other comparative methods used in the examples are referred to as "hot process technologies" (Comparative Method I and II)

Comparative Method I comprises the steps of hydrolysis, oxidation followed by precipitation, washing and drying. Hydrolysis is carried out at a temperature of 85° C. while oxidation is carried out at a temperature of 65° C. This process is described in detail in WO98/33822 the contents of which are herein incorporated in detail.

Comparative Method II comprises the same steps as Comparative Method I except that ca. three times smaller batch sizes are used.

An outline of Comparative Method I and II are given in Examples 3a and 3b.

Example 1

Preparation of MDOC Using the Cold Process of the Invention

In this example, the raw material for preparing a salt of microdispersed polyanhydroglucuronic acid were cotton linters containing 99.1% b/w (by weight) of α-cellulose and oxidised in 60% nitric acid with an admixture of 3.6% nitrous acid at a temperature of 28° C. in analogy with the procedure of GBP 709684.

Supply 600 l of demineralised water to the reactor, add the 28 kg of Sodium Hydroxide and cool down the formed solution to 20-25° C. while stirring. Prepare solution of Calcium Chloride, hexahydrate, in a polyethylene container, mix 80 l of demineralised water and 54 kg of Calcium Chloride, hexahydrate. Add progressively 140 kg of raw Oxidised Cellulose, prepared from the above defined raw material and dried out at 80° C. for 3 hours to the reactor, which then contains 140 kg dry matter, stirring constantly. During the dosage hold the temperature between 20 and 25° C. The suspension in the reactor discolours during the dosage to a yellow hue. Stir for at least 30 min after a last dosage of Oxidised Cellulose. Filter the reaction mixture. For approximately 40 min add progressively the entire amount of Calcium Chloride solution using a graduated vessel, while stirring and then stir the reaction mixture for another 45 min at a temperature between 20 and 25° C. For approximately 30 min add carefully the entire amount (36 l) of Hydrogen Peroxide using a graduated vessel. The temperature of the reaction mixture should not exceed 25° C. Then stir the suspension for a further 30 min at a temperature between 20 and 25° C. The suspension discolours to a snowy white hue. Adjust the pH of the reaction mixture by means of Hydrochloric Acid until a pH between 4.0 and 4.8 is attained. Stir the mixture for 15 minutes after each Hydrochloric Acid addition. Supply 1000 l of Ethanol to the reactor using a graduated vessel, while permanently stirring. Stir formed suspension for another 15 min at a constant temperature between 20 and 25° C. Isolate the raw product by centrifuging the parent liquor off. Disperse the isolated filter cake using a Turrax stirrer in 400 l of water. Supply gradually during 30 min 650 l of Ethanol to the reactor using a graduated vessel while permanently stirring using the Turrax stirrer. Stir the formed suspension for another 30 min at a constant temperature between 20 and 25° C. Isolate the raw product by centrifuging the parent liquor off. Disperse the isolated filter cake using the Turrax stirrer in 800 l of Ethanol and stir the suspension for at least 120 minutes. Isolate the raw product by centrifuging the parent liquor off. Disperse the isolated filter cake using the Turrax stirrer in 800 l of isopropylalcohol. Isolate the raw product by centrifuging the parent liquor off and dry the filter cake in a tray drier at a temperature of 80° C. After 15 hours drying submit a sample for quality control to check the content of the dry matter. The drying is finished when the content of dry matter exceeds 93%. Mill the dried powder using an Alpine mill.

Example 2

Five batches of MDOC were produced at room temperature as described in Example 1. Production parameters and result of analyses are summarised in the following Tables 1 to 4.

Table 1 shows the amounts of components used. Table 2 shows the different production parameters used. Table 3 gives the results of chemical analyses of each of the batches prepared. Table 4 gives the amount of Residuum on a 50 μm sieve of the final dry product. The individual pack numbers within a batch correspond to separately packed and sampled drums.

TABLE 1

| Component | Lot No | | | | |
|---|---|---|---|---|---|
| | 1084 | 1088 | 1098 | 1105 | 1106 |
| NaOH [kg] | 27 | 28 | 28 | 28 | 28 |
| OC dry matter [kg] | 140 | 140 | 140 | 140 | 140 |
| CaCl$_2$•6H$_2$O [kg] | 54 | 54 | 54 | 54 | 54 |
| H$_2$O$_2$ [l] | 36 | 36 | 36 | 36 | 36 |
| HCl | 0.7 | 6.2 | 3 | 0.3 | 1 |
| water in total [l] | 680 | 680 | 680 | 680 | 680 |
| EtOH - recycled [l] | 1650 | 1650 | 1650 | 1650 | 1650 |
| water content in EtOH [% vol/vol] | 7.7 | 4.3 | 5.9 | 5.2 | 5.2 |
| EtOH - denatured [l] | 800 | 800 | 800 | 800 | 800 |
| isopropanol [l] | 800 | 800 | 800 | 800 | 1600 |

TABLE 2

| Parameter | Lot No | | | | |
|---|---|---|---|---|---|
| | 1084 | 1088 | 1098 | 1105 | 1106 |
| dosing of OC [min] | 105 | 140 | 210 | 180 | 195 |
| time of hydrolysis [min] | 75 | 30 | 30 | 40 | 40 |
| max temperature during hydrolysis [° C.] | 28 | 34 | 24 | 22 | 22 |
| pH after hydrolysis | 10 | 12 | 12 | 11 | 11 |
| time of ion exchange [min] | 75 | 65 | 70 | 60 | 65 |
| max temperature during ion exch. [° C.] | 22 | 24 | 22 | 22 | 20 |
| pH after ion exchange | 8.3 | 9.1 | 8 | 8 | 8 |
| time of oxidation [min] | 30 | 35 | 30 | 30 | 30 |
| max temperature during oxidation | 22 | 23 | 25 | 23 | 22 |
| pH after oxidation | 4.8 | 7.5 | 6.5 | 4.8 | 5.6 |
| adjusted pH by HCl | 4.17 | 4.50 | 4.30 | 4.5 | 4.4 |
| time of washing [min] | 35 | 30 | 30 | 30 | 50 |
| time of dehydration in EtOH [h] | 2 | 2 | 48 | 2 | 2 |
| time of dehydration in isopropanol [h] | 5 | 5 | 10 | 10 | 23 |
| suspension stirred by turrax during dehydration [h] | 1 | 5 | 0.5 | 10 | 23 |

TABLE 3

| tested parameter | expected | method | 1084 | 1088 | 1098 | 1105 | 1106 |
|---|---|---|---|---|---|---|---|
| pH of water extr. | 4.5 to 7.0 | AM-01 | 5.11 | 5.81 | 5.39 | 5.25 | 5.44 |
| nitrogen | 0.5% b/w max. | AM-03 | 0.14 | 0.09 | 0.11 | 0.12 | 0.14 |
| loss on drying | 15% b/w max. | AM-05 | 7.7 | 2.2 | 6.5 | 7.0 | 7.0 |
| COOH content | 16 to 24% b/w | AM-06 | 21.5 | 20.3 | 21.9 | 21.2 | 21.5 |
| calcium | 4 to 8% b/w | AM-07 | 5.8 | 6.8 | 6.4 | 6.2 | 6.2 |
| sodium | 1.5 to 3.5% b/w | AM-08 | 3.1 | 3.2 | 3.1 | 2.8 | 3.5 |
| iron | 100 ppm max. | AM-10 | 19 | 36 | 12 | 13 | 29 |
| lead | 2 ppm max. | AM-10 | 0.6 | 1.1 | 0.5 | 0.6 | 0.3 |
| cadmium | 0.1 ppm max. | AM-10 | 0.04 | 0.04 | 0.04 | 0.07 | 0.05 |

TABLE 4

| | Lot No | | | | | | | | | |
|---|---|---|---|---|---|---|---|---|---|---|
| | 1084 | | 1088 | | 1098 | | 1105 | | 1106 | |
| Pack. No | [kg] | [%] | [kg] | [%] | [kg] | [%] | [kg] | [%] | [kg] | [%] |
| 1 | 16.19 | 2.03 | 14.31 | 0.58 | 10.63 | 2.21 | 14.61 | 1.00 | 16.30 | 0.52 |
| 2 | 16.25 | 3.15 | 14.04 | 0.77 | 16.36 | 1.14 | 14.09 | 0.08 | 16.29 | 1.23 |
| 3 | 16.55 | 3.16 | 13.62 | 0.98 | 11.55 | 1.31 | 12.08 | 0.36 | 17.52 | 0.35 |
| 4 | 15.50 | 2.17 | 13.59 | 2.02 | 15.73 | 2.63 | 14.30 | 0.08 | 16.44 | 2.35 |
| 5 | 17.23 | 2.86 | 13.07 | 1.39 | 15.02 | 1.64 | 13.54 | 0.50 | 18.68 | 0.71 |
| 6 | 16.45 | 1.18 | 12.81 | 1.24 | 15.48 | 0.59 | 9.93 | 0.70 | 18.40 | 0.48 |
| 7 | 16.07 | 1.70 | 15.96 | 2.37 | 19.00 | 2.10 | 16.26 | 0.33 | 20.34 | 0.68 |
| 8 | 16.95 | 2.19 | 13.81 | 1.83 | 19.14 | 0.56 | 16.16 | 0.50 | 19.63 | 0.91 |
| 9 | 12.64 | 2.81 | 11.00 | — | | | 15.04 | 0.46 | | |
| 10 | 10.70 | 3.19 | | | | | 9.93 | 0.41 | | |
| in total | 154.3 | | 122.21 | | 122.91 | | 135.94 | | 145.9 | |

Figure 2:
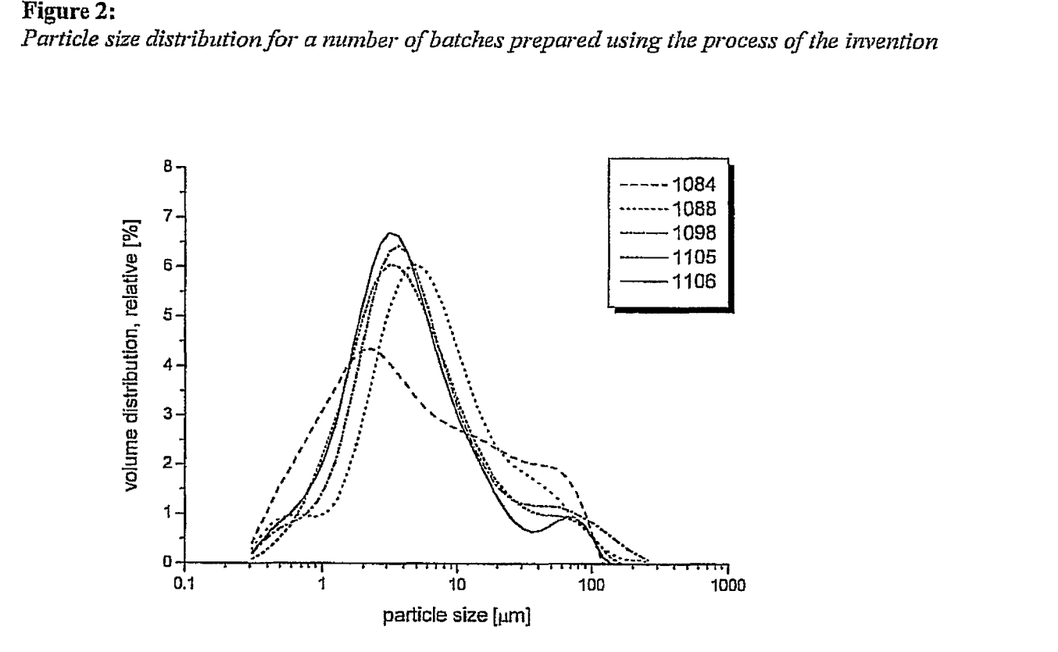
FIG. 2 is a graph showing the relative percentage of particle size distribution for a number of batches prepared using the process of the invention as determined by means of MASTERSIZER (Malvern Instruments Ltd. Ser. No. 34044-02, dispersant ethanol)

The data summarized in Tables 2 and 4 and the particle size distribution curves shown in FIG. 2 clearly indicate that increasing the time of high-shear (Turrax) stirring and higher overall time of dehydration favourably affect the particle size of the final product MDOC I designed for spray manufacture.

Example 3

Retrospective comparison was made of the cold process according to the present invention (Examples 1 and 2) and two versions of the original hot process (Comparative Methods I and II).

Example 3a

Comparative Method I (Example 1 from WO98/33822)

In this example, the raw material for preparing a salt of microdispersed polyanhydroglucuronic acid were cotton linters containing 99.1% b/w (by weight) of α-cellulose and oxidised in 60% nitric acid with an admixture of 3.6% nitrous acid at a temperature of 28° C. in analogy with the procedure of GBP 709684. The resulting product contained:

| | |
|---|---|
| carboxyl groups | 13.7% b/w |
| carbonyl groups | 4.2% b/w |
| bound nitrogen | 0.48% b/w |

In a 3000 ml laboratory mixer, 1000 ml of water and 0.158 g of calcium acetate were heated up to 60° C. and stirred at 600 rpm. After dissolution of calcium acetate, 2 g of the above defined oxidised cotton linters containing about 8% of volatile matter were added, temperature increased to 98° C., and the mixture stirred at 2800 rpm for 15 minutes while maintaining the temperature. The temperature was then decreased back to 60° C., pH adjusted to 8.5 by adding sodium hydroxide solution, 25 g of 30% hydrogen peroxide were added, and the hydrolysis continued at the reduced temperature for another 15 minutes. Subsequently the reaction system was cooled down to 40° C., stirring reduced to 300 rpm, and 1500 ml of 92% ethanol were added stepwise during about 10 minutes. The resulting colloid dispersion solution was then filtered, the residue was dispergated into 50% water-ethanol mixture and allowed to stand for one hour. After another filtration the residue was redispergated into 100 ml of isopropanol and allowed to stand for 6 hours. The same procedure was repeated once more, and then the product was filtered and dried in a vacuum drier at a temperature of 40° C.

An analysis of the product obtained yielded:

| | |
|---|---|
| loss on drying | 1.25% b/w |
| carboxyl group content | 16.8% b/w |
| carbonyl groups | 0.5% b/w |
| bound nitrogen content | 0.13% b/w |
| calcium content | 2.1% b/w |
| sodium content | 5.2% b/w |
| particle size | 2 to 5 μm |
| specific surface area | 98 $m^2/g$ |
| Molecular weight | $6 \times 10^4$ Daltons |

The product can be used directly as a hemostatic powder or as a component of an aerosol powder spray.

Example 3b

Comparative Method I (Example 2 from WO98/33822)

The raw material used was prepared via oxidation of a microbial (1→6)-βD-gluco-(1→3)-βD-glucane by gaseous nitrogen oxides, produced in a reaction of dried solid sodium nitrite with 75% b/w nitrous acid, and contained:

| | |
|---|---|
| carboxyl groups | 17.3% b/w |
| carbonyl groups | 1.3% b/w |
| bound nitrogen | 0.44% b/w |

In a 1500 ml laboratory mixer, 500 ml of water and 80 g of the air-dried oxidised raw material were mixed together and stirred at 250 rpm. 12 g of sodium peroxide were added gradually while stirring. The stirrer revolutions were then set at 1800 rpm and the system was maintained at a temperature of 52° C. for 30 minutes. The temperature was then decreased to 35° C., stirrer set at 120 rpm, pH adjusted to 6.0 by adding sodium hydroxide solution, 480 ml of 92% ethanol were added, and the system stirred at 800 rpm for 5 minutes. Subsequently the reaction system containing a colloid dispersion of sodium salt of D-glucurono-(1→6)-βD-gluco-(1→3)-βD-glucane was filtered and the residue was dialysed for 4 days against pure water. The dialysed product was redispergated into 500 ml of 80% ethanol and filtered again. The residue was redispergated into 400 ml of isopropanol and allowed to stand for 24 hours. Finally, the product was filtered and dried in a vacuum drier at a temperature of 40° C.

62 g of the product were obtained with the following characteristics:

| | |
|---|---|
| loss on drying | 2.3% b/w |
| carboxyl group content | 18.9% b/w |
| carbonyl groups | 1.1% b/w |
| bound nitrogen content | <0.1% b/w |
| calcium content | 2.1% b/w |
| sodium content | 6.99% b/w |
| particle size | 10 to 20 μm |
| specific surface area | 28 m$^2$/g |
| Molecular weight | Daltons |

The product can be used directly as a hemostatic powder, possibly as an active component of an aerosol formulation, and/or possibly as an active component in cosmetic formulations and the like.

Table 5 gives the average values of chemical parameters of batches of original procedure.

TABLE 5

| Tested parameter | Expected | Method | Cold Process 5 batches | Comparative Method I 62 batches | Comparative Method II 35 batches |
|---|---|---|---|---|---|
| pH of water extract | 4.5 to 7.0 | AM-01 | 5.40 ± 0.24 | 6.01 ± 0.54 | 6.30 ± 0.37 |
| Nitrogen | 0.5% b/w max. | AM-03 | 0.12 ± 0.02 | 0.14 ± 0.08 | 0.09 ± 0.03 |
| Loss on Drying | 15% b/w max. | AM-05 | 6.1 ± 2.0 | 5.0 ± 1.8 | 6.8 ± 1.1 |
| Carboxyl Content | 16 to 24% b/w | AM-06 | 21.2 ± 0.5 | 18.7 ± 1.3 | 19.5 ± 1.1 |
| Calcium | 4 to 8% b/w | AM-07 | 6.3 ± 0.3 | 6.2 ± 0.3 | 6.6 ± 0.3 |
| Sodium | 1.5 to 3.5% b/w | AM-08 | 3.1 ± 0.2 | 2.3 ± 0.4 | 2.7 ± 0.3 |
| Iron | 100 ppm max. | AM-10 | 22 ± 9 | 25 ± 13 | 27 ± 9 |
| Lead | 2 ppm max. | AM-10 | 0.6 ± 0.3 | 0.4 ± 0.2 | 0.6 ± 0.2 |
| Cadmium | 0.1 ppm max. | AM-10 | 0.05 ± 0.01 | 0.04 ± 0.04 | 0.04 ± 0.03 |

Figure 3:
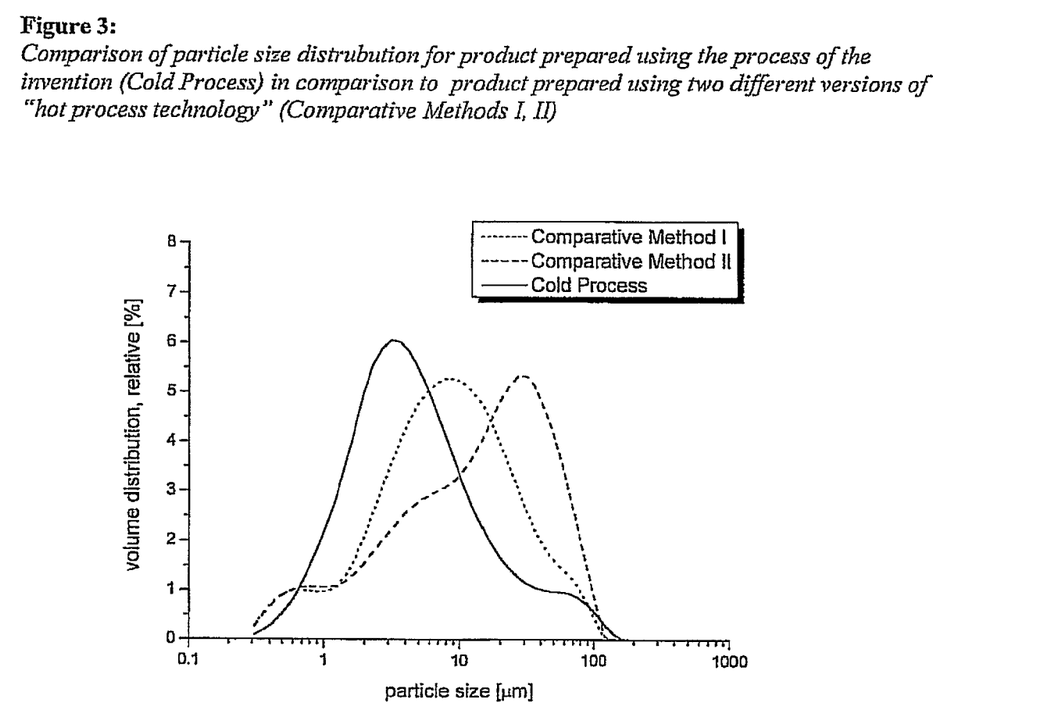
FIG. 3 is a graph showing the difference between the particle size distribution of a product prepared using the process of the invention (Cold Process) in comparison to a product prepared using two different versions of "hot process technology" (Comparative Method I and II).

FIG. 3 shows a comparison of randomly chosen samples of oxidized cellulose prepared by Comparative Method I and Comparative Method II and OC produced by the method of the present invention. Table 6 shows the differences between the method of the invention and Comparative Method I and II.

TABLE 6

| | Average yield of MDOC [%] | Average bulk volume [ml/g] |
|---|---|---|
| Comparative Method I | 85.8 | 14.2 ± 1.0 |
| Comparative Method II | 79.4 | 6.4 ± 1.4 |
| Cold Process (laboratory batches dried using tray drier) | 97.2 | 15.1 ± 1.2 |
| Cold Process (production batches dried using rotary vacuum dryer) | 94.1 | 6.6 ± 0.7 |

Example 4

Preparation of MDOC II Using Cold Process of the Invention

Supply 1050 l of demineralised water to the reactor, add the 40 kg of Sodium Hydroxide and cool down the formed solution to 20-25° C. while stirring. Prepare solution of Calcium Chloride, hexahydrate, in a polyethylene container, mix 60 l of demineralised water and 73.00 kg of Calcium Chloride, hexahydrate. Add progressively 350 kg of raw Oxidised Cellulose, prepared as per Example 1 and moistened with 40% by weight of concentrated ethanol, to the reactor, which thus contains 210 kg dry matter, stirring constantly. During the dosage hold the temperature between 20-25° C. The suspension in the reactor discolours during the dosage to a yellow hue. Stir for at least 30 min after a last dosage of Oxidised Cellulose. Filter the reaction mixture. For approximately 30 min add progressively the entire amount of Calcium Chloride solution using a graduated vessel, while stirring and then stir the reaction mixture for another 45 min at a temperature between 20 and 25° C. For approximately 30 min add carefully the entire amount (54 l) of Hydrogen Peroxide using a graduated vessel. The temperature of reaction mixture should not exceed 25° C. Then stir the suspension for a further 30 min at a temperature between 20 and 25° C. The suspension discolours to a snowy white hue. Adjust the pH of the reaction mixture by means of Hydrochloric Acid until a pH between 4.0 and 4.5 is attained. Stir the mixture for 15 minutes after each Hydrochloric Acid addition. Supply 1500 l of Ethanol to the reactor using a graduated vessel, while permanently stirring. Stir the formed suspension for another min at a constant temperature between 20 and 25° C. Isolate the raw product by centrifuging the parent liquor off. Disperse the isolated filter cake using a Turrax stirrer in 1000 l of water. Supply gradually for 30 min 1400 l of Ethanol to the reactor using a graduated vessel while permanently stirring using the Turrax stirrer. Stir the formed suspension for another 30 min at the constant temperature between and 25° C. Isolate the raw product by centrifuging the parent liquor off. Disperse the isolated filter cake using the Turrax stirrer in 900 l and add 1100 l of Ethanol to the reactor using a graduated vessel and stir the suspension for at least 60 minutes. Isolate the raw product by centrifuging the parent liquor off and dry the filter cake in a rotary vacuum drier at a temperature of 80° C. in the vacuum. After 15 hours drying submit a sample for quality control to check the content of the dry matter. The drying is finished when the content of the dry matter exceeds 93%. Fractionate the product on a sieve screening machine to obtain particle size of between 90 and 400 μm.

Example 5

Three batches of MDOC II were produced at room temperature as described in Example 4. Production parameters and the result of analyses are summarised in the Tables 7 to 10.

Table 7 outlines the amounts of components used. Table 8 outlines the different production parameters used. Table 9 gives the results of chemical analyses of each of the batches prepared. Table 10 outlines the yields obtained.

TABLE 7

| | Lot No | | |
|---|---|---|---|
| Component | 2070 | 2080 | 2081 |
| NaOH [kg] | 40 | 40 | 40 |
| OC dry matter [kg] | 210 | 210 | 210 |
| CaCl$_2$•6H$_2$O [kg] | 73 | 73 | 73 |
| H$_2$O$_2$ [l] | 54 | 54 | 54 |
| HCl | 5.0 | 1.5 | 1.5 |
| water in total [l] | 2800 | 3350 | 3350 |
| EtOH - recycled [l] | 4200 | 4000 | 4000 |
| water content in rec. EtOH [% vol/vol] | 7.3 | 6.0 | 5.4 |

TABLE 8

| | Lot No | | |
|---|---|---|---|
| Parameter | 2070 | 2080 | 2081 |
| time of hydrolysis [min] | 30 | 30 | 30 |
| max temperature during hydrolysis [° C.] | 30 | 25 | 25 |
| pH after hydrolysis | 11 | 10 | 11 |
| time of ion exchange [min] | 45 | 45 | 45 |
| max temperature during ion exch. [° C.] | 25 | 25 | 25 |
| pH after ion exchange | 10 | 8 | 8 |

TABLE 8-continued

| | Lot No | | |
|---|---|---|---|
| Parameter | 2070 | 2080 | 2081 |
| time of oxidation [min] | 30 | 30 | 30 |
| max temperature during oxidation | 30 | 23 | 25 |
| pH after oxidation | 6.7 | 5.5 | 5.7 |
| adjusted pH by HCl | 4.44 | 4.69 | 4.40 |
| ratio water/EtOH during the last washing | 0.66 | 1 | 1 |

TABLE 9

| Tested Parameter | Expected | Method | 2070 | 2080 | 2081 |
|---|---|---|---|---|---|
| pH of water extr. | 4.5 to 7.0 | AM-01 | 5.58 | 5.23 | 5.08 |
| Nitrogen | 0.5% b/w max. | AM-03 | 0.10 | 0.09 | 0.09 |
| Loss on Drying | 15% b/w max. | AM-05 | 3.0 | 7.5 | 7.0 |
| Caroxyl Content | 16 to 24% b/w | AM-06 | 22.3 | 18.5 | 21.9 |
| Calcium | 4 to 8% b/w | AM-07 | 6.0 | 6.1 | 6.0 |
| Sodium | 1.5 to 3.5% b/w | AM-08 | 3.1 | 2.7 | 2.5 |
| Iron | 100 ppm max. | AM-10 | 41 | 31 | 23 |
| Lead | 2 ppm max. | AM-10 | 0.6 | 0.7 | 0.8 |
| Cadmium | 0.1 ppm max. | AM-10 | 0.04 | 0.04 | 0.08 |

TABLE 10

| | Lot No: | | |
|---|---|---|---|
| | 2070 | 2080 | 2081 |
| middle fraction (90-400 μm) [kg] | 106.75 | 154.01 | 157.98 |
| undersize (<90 μm) [kg] | 59.57 | 35.78 | 32.81 |
| oversize (>400 μm) [kg] | 2.62 | 2.63 | 2.58 |
| total yield [kg] | 168.94 | 192.42 | 190.37 |

The data summarized in Tables 7 and 10 clearly show that increasing water content in the washing mixture favourably affect the agglomeration of the final product MDOC II designed for plaster manufacture.

For agglomerates production (MDOC II) it is better to use a rotary vacuum drier and for powder production (MDOC I) a tray drier is more suitable. The water content in the filter cake before drying plays a major role in the particle size of the final product.

Example 6

Retrospective comparison was made of the cold process according to the present invention (Examples 4 and 5) and the hot process (Comparative Methods I and II for MDOC II production).

Table 11 gives the average values of chemical parameters of batches of original procedure. Table 12 shows the differences between the method of the invention and Comparative Method I and Comparative Method II for the MDOC II.

TABLE 11

| Tested parameter | Expected | Method | Cold Process 5 batches | Comparative Method I 22 batches | Comparative Method II 36 batches |
|---|---|---|---|---|---|
| pH of water extract | 4.5 to 7.0 | AM-01 | 5.2 ± 0.2 | 6.1 ± 0.6 | 6.3 ± 0.8 |
| Nitrogen | 0.5% b/w max. | AM-03 | 0.11 ± 0.02 | 0.15 ± 0.07 | 0.10 ± 0.03 |
| Loss on Drying | 15% b/w max. | AM-05 | 6.5 ± 1.6 | 5.1 ± 1.9 | 5.8 ± 1.4 |
| Carboxyl Content | 16 to 24% b/w | AM-06 | 22.0 ± 1.9 | 19.6 ± 1.2 | 20.1 ± 1.2 |
| Calcium | 4 to 8% b/w | AM-07 | 6.1 ± 0.1 | 5.4 ± 0.4 | 6.1 ± 0.8 |
| Sodium | 1.5 to 3.5% b/w | AM-08 | 2.8 ± 0.2 | 2.5 ± 0.4 | 2.6 ± 0.4 |

TABLE 11-continued

| Tested parameter | Expected | Method | Cold Process 5 batches | Comparative Method I 22 batches | Comparative Method II 36 batches |
|---|---|---|---|---|---|
| Iron | 100 ppm max. | AM-10 | 26 ± 9 | 26 ± 18 | 26 ± 11 |
| Lead | 2 ppm max. | AM-10 | 0.7 ± 0.1 | 0.4 ± 0.3 | 0.6 ± 0.3 |
| Cadmium | 0.1 ppm max. | AM-10 | <0.05 | <0.05 | <0.05 |

TABLE 12

| | Yield of fraction MDOC (90-400 µm) [%] | Total Yield [%] |
|---|---|---|
| Comparative Method I | 45.7 | 84.0 |
| Comparative Method II | 40.1 | 73.0 |
| Cold Process | 66.5 | 87.6 |

Hydrolysis and implicit ion-exchange in the process described in WO98/33822 take place simultaneously in a heterogeneous system since the raw oxidised cellulose is almost completely insoluble in water and most of the resulting products—binary or higher salts of PAGA—are only partially soluble in water; in other words, both the reactant and products form a permanent "liquid-solid" heterogeneous system. Due to this fact higher temperatures are needed to achieve sufficient reaction rates and thereby reasonable reaction times. Further, the resulting ratio of PAGA bound cations cannot be controlled and only depends on physicochemical equilibrium established in the reaction system.

In contrast, in the process of the invention after the hydrolysis of raw oxidised cellulose a homogeneous system is formed The reaction can be carried out at a low temperature. Subsequent ion-exchange can also take place at low temperature due to low degree of heterogeneity (in this case, heterogeneity of the system is given only by binary—or higher—PAGA salts being formed). Further, the resulting ratio of cations is directly controllable by input weight of second (or additional) salt (base).

This leads to even further benefits as follows

Use of lower reaction temperatures reduces degradation of oxidised cellulose and thereby increases product yield (Example 3, Table 6, and Example 6, Table 11)

Use of lower reaction temperatures results in reduction of production time/costs (heating and cooling down of reaction vessel during the production)

Homogeneous hydrolysis suppresses dependence on stirring conditions and makes easier upscaling of production process (compare processed amount of raw oxidised cellulose in Example 1 vs. Example 5)

Homogeneous hydrolysis enables subsequent filtration to remove unoxidised cellulose introduced in raw oxidised cellulose and thereby increases product purity The term "suitable" polysaccharide refers throughout to a polysaccharide that due to its chemical nature can serve as starting raw material for preparing PAGA.

The invention is not limited to the embodiments hereinbefore described but may be varied in detail.

REFERENCES

1. Burchard W. Ed., Polysaccharide, Eigenschaften and Nutzung, Springer Verlag, Berlin 1985, p. 144
2. Kenyon et al., Ind. Eng. Chem., 41, No 1, 2-8 (1949)
3. Painter J. et al., Carbohydrate Research 140, 61 (1985);
4. Alhaique F., Chim. Oggi 11-15, 17 (1986)
5. Kaversneva E. P., Doklady A N SSSR (U.S.S.R.) 78 (3), 481 (1951);
6. Nevell T. P., J. Text. Ind. 42, 91 (1951);
7. Sihtola M. et al., J. Polym. Sci, Part C, (2), 289 (1963);
8. Pastéka M., Chemické Zvesti (Slovakia) (20), 855 (1966)
9. Saito T., Isogai A., Biomacromolecules 5 (5), 1983 (2004);
10. Li et al., Oxidaton of primary alcohols to carboxylic acids with a TEMPO catalyst using $NaClO_2$ and NaClO

The invention claimed is:

1. A method for preparing polyanhydroglucuronic acid salts comprising the steps of:
hydrolysis of a polyanhydroglucuronic acid-containing material in the presence of an inorganic and/or organic salt or base to form a homogenous solution comprising a fully hydrolysed salt of polyanhydroglucuronic acid; and
subsequently subjecting the homogenous solution formed by the hydrolysis step to ion exchange in the presence of one or more water soluble and/or partially soluble inorganic and/or organic salt or base with a different cation from the inorganic and/or organic salt or base used in the hydrolysis step to form a binary or higher salt of polyanhydroglucuronic acid, the method being carried out at a temperature of from 15° C. to 30° C.;
wherein the hydrolysis is carried out in an aqueous solution;
wherein the inorganic and/or organic salt and/or base used in the hydrolysis step is selected from the group consisting of any one or more of chlorides, sulphates, carbonates, formates, acetates or alkali and/or alkaline earth metals, hydroxides of alkali and/or alkaline earth metals, alkylamines and alkanolamines, in concentrations ranging from 0.001 to 5 mol/1;
wherein the water soluable and/or partially soluble inorganic and/or organic salt and/or base used in the ion exchange step is selected from the group consisting of any one or more of hydroxides, chlorides, nitrates, borates, sulphides, sulphates and acetates;
wherein hydrolysis is carried out for a period of from 15 to 30 minutes; and
wherein ion exchange is carried out for a period of from 15 to 30 minutes.

2. The method as claimed in claim 1 wherein the polyanhydroglucuronic acid-containing material is obtained by oxidation of a polysaccharide.

3. The method as claimed in claim 2 wherein the polyanhydroglucuronic acid-containing material is obtained by oxidation with nitrogen oxides or using sodium hypochorite in the presence of a 2,2,6,6-tetramethylpiperidine-1-oxyl radical catalyst.

4. The method as claimed in claim 1 comprising supplemental oxidation of the product of the ion exchange step in the presence of one or more of organic and inorganic peroxides.

5. The method as claimed in claim 1 wherein the aqueous solution comprises an admixture of an organic solvent.

6. The method as claimed in claim 5 wherein the organic solvent is selected from the group consisting of any one or more of ethanol, isopropanol and other water-miscible alcohol or organic solvents.

7. The method as claimed in claim 4 wherein supplemental oxidation is carried out for a period of from 15 to 30 minutes.

8. The method as claimed in claim 1 further comprising the step of precipitating, washing and drying the product.

9. The method as claimed in claim 1 further comprising the step of dehydrating the product.

10. The method as claimed in claim 8 wherein the pH is adjusted to between 2.0 and 8.5 prior to concentration.

11. The method as claimed in claim 8 wherein the product is washed and/or dehydrated, using water miscible or partially miscible organic solvents and/or converted, in an appropriate manner, for intended subsequent use.

12. The method as claimed in claim 7 wherein the product is dried at a temperature of between 20 and 105° C.

13. The method as claimed in claim 12 wherein after drying, the product is milled and/or sieved.

14. The method as claimed in claim 4 wherein an oxidative environment during supplemental oxidation is established by the presence of oxidising agents selected from the group consisting of one or more of hydrogen, sodium or magnesium peroxide, peroxoacids and their salts, hypochlorites and chlorites.

15. The method as claimed in claim 2 wherein the polysaccharide is selected from the group consisting of native or regenerated cellulose and starch.

* * * * *

UNITED STATES PATENT AND TRADEMARK OFFICE
CERTIFICATE OF CORRECTION

PATENT NO. : 8,445,671 B2  
APPLICATION NO. : 11/991153  
DATED : May 21, 2013  
INVENTOR(S) : Dvoř\ak et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 820 days.

Signed and Sealed this
Eighth Day of September, 2015

Michelle K. Lee
*Director of the United States Patent and Trademark Office*